United States Patent
Crystal et al.

(10) Patent No.: US 6,329,348 B1
(45) Date of Patent: Dec. 11, 2001

(54) METHOD OF INDUCING ANGIOGENESIS

(75) Inventors: Ronald G. Crystal, Potomac, MD (US); Todd K. Rosengart, Highland Park, IL (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/436,940

(22) Filed: Nov. 8, 1999

(51) Int. Cl.$^7$ .......................... A61K 48/00; A61K 38/00; C12N 15/63; C12N 15/86; C07K 1/00

(52) U.S. Cl. ..................... 514/44; 514/2; 435/320.1; 435/455; 435/456; 530/350; 530/399

(58) Field of Search .................... 424/93.2; 435/456, 435/455, 320.1, 375, 325; 536/23.1, 23.5, 23.51; 514/44, 2; 530/350, 399

(56) References Cited

U.S. PATENT DOCUMENTS

| | | | |
|---|---|---|---|
| 4,296,100 | 10/1981 | Franco ........................... | 424/108 |
| 5,776,755 | 7/1998 | Alitalo et al. . | |
| 5,797,870 | 8/1998 | March et al. .................. | 604/49 |
| 5,830,879 | 11/1998 | Isner ............................. | 514/44 |
| 5,851,999 | 12/1998 | Ullrich et al. . | |
| 5,869,037 | 2/1999 | Crystal et al. ................ | 424/93.2 |
| 5,879,713 | 3/1999 | Roth et al. .................... | 424/489 |
| 5,902,583 | 4/1999 | Buchsbaum et al. . | |
| 5,932,540 | 8/1999 | Hu et al. ....................... | 514/2 |
| 5,941,868 | 8/1999 | Kaplan et al. ................ | 604/500 |
| 5,944,710 | 8/1999 | Dev et al. ..................... | 604/500 |
| 5,972,639 | 10/1999 | Parandoosh .................. | 435/29 |
| 5,976,782 | 11/1999 | Parish et al. .................. | 435/4 |
| 5,993,444 | 11/1999 | Ammar et al. ................ | 606/21 |
| 6,011,009 | 1/2000 | Goldberg et al. ............. | 514/8 |
| 6,090,618 | 7/2000 | Parmacek et al. ............ | 435/320.1 |
| 6,100,242 | 8/2000 | Hammond et al. ........... | 514/44 |
| 6,120,799 | 9/2000 | McDonald et al. ........... | 424/450 |
| 6,121,246 | 9/2000 | Isner ............................. | 514/44 |
| 6,123,084 | 9/2000 | Jandak et al. ................. | 128/898 |
| 6,133,231 | 10/2000 | Ferrara et al. ................ | 514/2 |

FOREIGN PATENT DOCUMENTS

WO 98/32859    7/1998   (WO) .
WO 99/44656
       A        9/1999   (WO) .

OTHER PUBLICATIONS

Goldman et al., *Proc. Natl. Acad. Sci. USA*, 95:8795–800, Jul. (1998).
Achen et al., *Int. J. Exp. Path.*, 79, 255–265 (Jun. 1998).
Bauters et al., *Circulation*, 91 (11), 2802–2809 (Jun. 1995).
Carmeliet et al., *Curr. Top. Microbio.l Immunol.*, 237(–HD):133–58 (Apr. 1999).
Del Rio et al., *Gene Therapy*, 6, 1734–1741 (May 1999).
Diaz–Flores et al., *Experientia* 52(1), 25–30 (Jan. 1996).
Dichek et al., *Circulation*, 80(5), 1347–1353 (Nov. 1989).
Fasol et al., *J. Mol. Cell Cardiol.* 24 (Supplement I), S83 (Sep. 1993).
Ferrara, *J. Mol. Med.*, 77, 527–543 (Jul. 1999).
Ferrara, *Kidney International*, 56, 794–814 (Jun. 1999).
Flugelman et al., *J. Mol. Cell Cardiol.* 24, (Supplement I), S83 (Sep. 1993).
Flugelman et al., *Circulation Research*, 70, (2), 348–352 (Feb. 1992).
Folkman et al., *Nature*, 329, 671–672 (Oct. 1987).
Giordano et al., *Nature Medicine*, 2 (5), 534–539 (May 1996).
Isner, *Am. J. of Card.*, 82(10A), 635–636 (Nov. 1998).
Kawakami et al., *Brain Res.*, 697 (1–2), 104–111 (Oct. 1995).
Lynch et al., *J. Biol. Chem.* 13 (274), 8455–8459 (Mar. 1999).
Melillo et al., *Cardiovascular Res.* 35, 480–489, (Jun. 1997).
Mesri et al., *Circulation Res.*, 76 (2). 161–167 (Feb. 1995).
Pu et al., *Circulation*, 88(1), 208–215 (Jul. 1993).
Rosengart et al.,*J. Vasc. Surg.* 26 (2), 302–312 (Aug. 1997).
Rosenstein et al., *Proc. Natl. Acad. Sci. USA*, 95 (12), 7086–7091 (Jun. 1998).
Suri et al., *Cell*, 87, 1171–1180 (Dec. 1996).
Takeshita et al., *J. Clin. Invest.*, 93, 662–670 (Feb. 1994).
Tsurumi et al., *Circulation*, 94 (12) 3281–3290 (Dec. 1996).
Yamamoto et al., *Circulation*, 94 (supplement 1), I–637 (Feb. 1996).
Zachary et al., *Arterioscler Throm Vasc Biol.*, (20), 1512–1520 (Nov. 1999).
Crystal, Presentation at American Heart Association 72$^{nd}$ Scientific Sessions, Atlanta Georgia (Nov. 6, 1999).
Melillo et al. Gene therapy for collateral vessel develoment. Cardiovascular Research. vol. 353, No. 3, pp. 480–489, 1997.*
Lewis et al. Angiogenesis by gene therapy: a new horizon for myocardial revascularization? Cardiovascular Research. vol. 35, No. 3, pp. 490–497, 1997.*
Lee et al. Gene therapy for therapeutic myocardial angiogenesis: a promising synthesis of two emerging technologies. Nature Medicine. vol. 4, No. 6, pp. 739–742, 1998.*
W. French Anderson. Human gene therapy. Nature. vol. 392, pp. 25–30, 1998.*
Verma et al. Gene therapy–promises, problems and prospects. Nature. vol. 389, pp. 239–242, 1997.*

(List continued on next page.)

*Primary Examiner*—Dave T. Nguyen
*Assistant Examiner*—Quang Nguyen
(74) *Attorney, Agent, or Firm*—Leydig, Voit & Mayer, Ltd.

(57) ABSTRACT

The present invention provides a method for enhancing the level of perfusion of blood to a target location in a host comprising establishing a gradient of an angiogenic mediator of increasing concentration from a source location (e.g., an angiogenically functional location) in the host to a target location (e.g., an angiogenically dysfunctional location) in the host, such that the level of perfusion of blood to the target location in the host is enhanced.

21 Claims, No Drawings

OTHER PUBLICATIONS

Losordo et al·Gene Therapy for Myocardial Angiogenesis·Initial Clinical Results with Direct Myocardial Injection of phVEGF$_{165}$ as Sole Therapy for Myocardial Ischemia·Circulation·22/29 1998 pp. 2800–2804.*

Mack et al·Cardiopulmonary Support and Physiology·The Journal of Thoracic and Cardiovascular Surgery·vol. 115, No. 1, pp. 168–177. 1998.*

Dang et al.; Gene Therapy and Translational Cancer Research, 1999, Clinical Cancer Research, vol. 5: 471–474.

Deonarain; Ligand–targeted receptor–mediated vectors for gene delivery, 1998. Exp. Opin. Ther. Patents 8: 53–69.

* cited by examiner

METHOD OF INDUCING ANGIOGENESIS

TECHNICAL FIELD OF THE INVENTION

The present invention relates to a method for enhancing the level of perfusion of blood to a target tissue, a method for treating a target tissue suffering from or at risk of suffering from ischemic damage, and a method of inducing angiogenesis in a target tissue.

BACKGROUND OF THE INVENTION

Angiogenesis, the growth of new blood vessels, is a complex process involving the disruption of vascular basement membranes, migration and proliferation of endothelial cells, and subsequent blood vessel formation and maturation. Several mediators are known to elicit angiogenic responses, and administration of these mediators promotes revascularization of ischemic tissues. Vascular endothelial growth factor (VEGF protein) is one of the most specific of the known angiogenic mediators due to localization of its receptors almost exclusively on endothelial cells. Receptors for VEGF are upregulated under ischemic conditions, and the administration of recombinant VEGF augments the development of collateral vessels and improves function in peripheral and myocardial ischemic tissue.

The delivery of VEGF protein remains a significant challenge. The half-life of VEGF protein is very short; the administration of high doses of VEGF protein is associated with hypotension, and systemic administration of VEGF protein can cause promiscuous induction of angiogenesis in tissues other than that which has been targeted. Promiscuous induction of angiogenesis can cause blindness, increase the aggressiveness of tumor cells, and lead to a multitude of other negative side-effects. Furthermore, the quantity of VEGF protein delivered is important. If too little VEGF protein is delivered, angiogenesis will not be induced, and a significant therapeutic benefit will not be achieved. If too much VEGF protein is delivered, the formation of disorganized vasculature beds, loss of function in the affected tissue, and promiscuous angiogenesis can result.

Attempts to address these problems have utilized methods wherein multiple applications of an angiogenic mediator were made to a target tissue. For example, International Patent Application WO 98/32859 discloses methods of inducing angiogenesis comprising multiple applications of a pharmaceutical composition comprising (a) a pharmaceutically acceptable carrier and (b) an adenoviral vector comprising a DNA encoding an angiogenic peptide, such that the level of perfusion of blood to the target tissue is enhanced.

There remains a need, however, for improved methods of inducing angiogenesis in a target tissue. The present invention provides such a method. These and other advantages of the present invention, as well as additional inventive features, will be apparent from the description of the invention provided herein.

BRIEF SUMMARY OF THE INVENTION

The present invention provides a method for enhancing the level of perfusion of blood to a target location in a host. The method comprises establishing a gradient of an angiogenic mediator of increasing concentration from a source location in the host to a target location in the host, such that the level of perfusion of blood to the target location in the host is enhanced.

DETAILED DESCRIPTION OF THE INVENTION

The invention may best be understood with reference to the following detailed description of the invention which focuses on the preferred embodiments. The present invention provides a method for enhancing the level of perfusion of blood to a target location in a host. The method comprises establishing a gradient of an angiogenic mediator of increasing concentration from a source location in the host to a target location in the host, such that the level of perfusion of blood to the target location in the host is enhanced.

Angiogenic Mediator

An "angiogenic mediator" can be any substance that enhances the level of perfusion of blood to a location, particularly by initiating or enhancing angiogenesis (i.e., the formation of new blood vessels or neovascularization, as well as the promotion of blood vessel formation, including collateral blood vessel growth). Therefore, an angiogenic mediator is any substance that will induce the initiation of angiogenesis to a location not otherwise undergoing angiogenesis or enhance or heighten angiogenesis to a location already undergoing angiogenesis.

The angiogenic mediator can be any suitable angiogenic mediator. Examples of angiogenic mediators include angiogenic peptides. More particularly, a number of peptides broadly classified as "growth factors" are known to induce angiogenesis. Suitable examples of such growth factors include Fibroblast Growth Factor (FGF) (more particularly, acidic Fibroblast Growth Factor (aFGF) and basic Fibroblast Growth Factor (bFGF)), Transforming Growth Factor (particularly, Transforming Growth Factor-Beta), Placental Growth Factor, Platelet-derived Endothelial Cell Growth Factor, and Vascular Endothelial Growth Factor (VEGF). Other angiogenic mediators include Angiogenin, and cytokines such as Tumor Necrosis Factor-alpha and Interleukin-8. The angiogenic mediator is not limited to peptides such as cytokines or growth factors, but includes other substances such as modified peptides (e.g., glycoproteins or lipoproteins), ribozymes, polynucleotides, and other substances that induce angiogenesis.

Another example of a suitable angiogenic mediator is a nucleic acid encoding an angiogenic substance. Desirably, such nucleic acid will be in the form of a vector comprising a DNA encoding the angiogenic substance, preferably a DNA encoding an angiogenic peptide. Preferably, the vector will comprise a viral vector. More preferably, the vector will comprise an adenoviral vector (i.e., a viral vector being at least partially comprised of a DNA sequence of (or similar to) that of an adenovirus). Through the use of such adenoviral vectors as angiogenic mediators, it is possible to infect host cells and thereby induce the sustained, predictable, and effective production of an angiogenic peptide for about a week. After about a week, the adenoviral vector ceases to produce the angiogenic peptide, and, to that extent, the present invention provides a self-terminating method of inducing angiogenesis.

Adenoviral vectors are preferred because, unlike plasmids and other viral vectors (e.g., herpes simplex virus), adenoviral vectors achieve gene transfer in both dividing and nondividing cells, with high levels of protein expression in cardiovascular relevant sites such as myocardium, vascular endothelium, and skeletal muscle. Furthermore, the gene transferred by an adenoviral vector functions in an epichromosomal position and thus carries little risk of inappropriately inserting the transferred gene into a critical site of the host genome. The adenoviral vector also desirably is deficient in at least one gene function required for viral replication. Preferably, the adenoviral vector is deficient in at least one essential gene function of the E1, E2, and/or E4 regions of the adenoviral genome. More preferably, the adenoviral vector is deficient in at least one essential gene function of the E1 region of the adenoviral genome (e.g., the E1a region and/or E1b region), alone or in combination with deficiencies of essential gene functions of other adenoviral genome regions. Most preferably, the vector additionally is deficient in at least part of the E3 region of the adenoviral genome (e.g., an XbaI deletion of the E3 region). Suitable replication deficient adenoviral vectors are disclosed in U.S. Pat. No. 5,851,806 and International Patent Application WO 95/34671. For example, suitable replication deficient adenoviral vectors include those with at least a partial deletion of the E1a region, at least a partial deletion of the E1b region, and at least a partial deletion of the E3 region. Alternatively, the replication deficient adenoviral vector can have a deletion of the entire E1 region, at least a partial deletion of the E3 region, and at least a partial deletion of the E4 region of the adenoviral genome.

Furthermore, the viral vector's coat protein can be modified so as to incorporate a specific protein binding sequence, as described in U.S. Pat. No. 5,432,075, or the viral vector's coat protein can be modified so as to decrease the viral vector's ability or inability to be recognized by a neutralizing antibody directed against the wild-type coat protein, as described in International Patent Application WO 98/40509.

The DNA encoding an angiogenic mediator (e.g., an angiogenic peptide such as VEGF) can be any suitable DNA molecule. The DNA desirably is operably linked to suitable expression signals. Whereas the DNA can be operably linked to any suitable set of expression signals, preferably, the expression of the DNA is under the control of the cytomegalovirus (CMV) immediate early promoter.

The DNA can encode any suitable angiogenic mediator. Preferably, the angiogenic mediator, is an angiogenic peptide. More preferably, the angiogenic peptide is a growth factor as described above, particularly a VEGF protein. Optimally the angiogenic peptide is selected from the group comprising $VEGF_{121}$, $VEGF_{145}$, $VEGF_{165}$, and $VEGF_{189}$, which are described in U.S. Pat. No. 5,332,671 (Ferrara et al.), U.S. Pat. No. 5,240,848 (Keck et al.), and U.S. Pat. No. 5,219,739 (Tischer et al.). Most preferably, because of their higher biological activity, the angiogenic peptide is $VEGF_{121}$ or $VEGF_{165}$, particularly $VEGF_{121}$. A notable difference between $VEGF_{121}$ and $VEGF_{165}$ is that $VEGF_{121}$ does not bind to heparin with a high degree of affinity as does $VEGF_{165}$. Generally, VEGF moieties are advantageous over other angiogenic peptides because VEGF proteins do not induce the growth of tissues not involved in the production of new vasculature. Other angiogenic peptides include VEGF II, VEGF-C, FGF-4, angiogenin, angiogenin-2, and P1GF, which are described in U.S. Pat. No. 5,338,840 (Bayne et al.) and U.S. Pat. No. 5,532,343 (Bayne et al.), International Patent Application WO 95/24473 (Hu et al.), European Patent Documents 476 983 (Bayne et al.), 506 477 (Bayne et al.), and 550 296 (Sudo et al.), and Japanese Patent Documents 1038100, 2117698, 2279698, and 3178996.

The adenoviral vector also can include a DNA encoding an angiogenic peptide receptor. Suitable angiogenic peptide receptors include, for example, FLT-1, FLK-1, and FLT-4. Indeed, in certain embodiments, the adenoviral vector can utilize a DNA encoding an angiogenic peptide receptor in place of, rather than in addition to, the DNA encoding an angiogenic peptide.

The DNA can be inserted into any suitable region of the adenoviral vector as an expression cassette. In that respect, the skilled artisan will readily appreciate that there are certain advantages to using an adenoviral vector deficient in some essential gene region of the adenoviral genome inasmuch as such a deficiency will provide room in the vector for a transgene and will prevent the virus from replicating in the absence of a complementary cell line. Preferably, the DNA segment is inserted into the E1 region of the adenoviral vector. Whereas the DNA segment can be inserted as an expression cassette in any suitable orientation in any suitable region of the adenoviral vector, preferably the orientation of the DNA segment is from right to left. By the expression cassette having an orientation from right to left, it is meant that the direction of transcription of the expression cassette is opposite that of the region of the adenoviral vector into which the expression cassette is inserted.

An adenoviral vector illustrative of the present inventive vector is deficient in the entire E1a region, at least part of the E1b region, and at least part of the E3 region of the adenoviral genome and contains the DNA encoding human $VEGF_{121}$ or human $VEGF_{165}$ under the control of the CMV immediate early promoter in the E1 region of the adenoviral genome. Such a vector supports in vivo expression of VEGF that is maximized at one day following administration and is not detectable above baseline levels as little as one week after administration. This is ideal inasmuch as it is sufficient to provide substantial growth of new vasculature while minimizing adverse neovascularization at distal sites. In that regard, when this vector is locally administered to a target tissue, no detectable VEGF expression can be detected in blood serum using standard ELISA monitoring assays.

Advantageously, local administration to a target tissue of adenoviral vectors encoding human $VEGF_{121}$ or $VEGF_{165}$ in the E1 region of the adenoviral genome are able to increase blood flow at least 3-fold in the extremities of mammals (e.g., the hindlimb of Sprague-Dawley rats) with iliac and femoral artery ligations.

Source and Target Locations

The target and source locations can be any suitable locations in a host that can be subject to administration of the angiogenic mediator within the context of the present invention. Preferably, the target and source locations comprise tissues (i.e., a target tissue and a source tissue), more preferably the target and source locations (e.g., tissues) comprise receptors capable of binding an angiogenic peptide, such as growth factor receptors. Even more preferably, the target and source tissues comprise VEGF receptors. Optimally, the source and target tissues comprise endothelial cells.

Generally, the source and/or target locations will comprise tissue(s) that is a part of, or forms, a discrete organ, e.g., a muscle, such as the heart. The source location preferably is an angiogenically functional location, e.g. a location in the host that has a sufficient level of perfusion of blood, such as an area near existing blood vessels (preferably with a significant amount of existing blood vessels). The target location preferably is an actual or potential angiogenically dysfunctional location, e.g., a location in the host that is either undergoing or is at risk of undergoing ischemia or any other condition wherein the growth of new, or extension of existing, blood vessels is desirable.

Typically, the target location (particularly an angiogenically dysfunctional location) will be suffering from or be at risk of suffering from ischemic damage, which results when the tissue is deprived of an adequate supply of oxygenated blood. The interruption of the supply of oxygenated blood is often caused by a vascular occlusion. Such vascular occlusion can be caused by arteriosclerosis, trauma, surgical procedures, disease, and/or other indications. There are many ways to determine if a tissue is at risk of suffering ischemic damage from undesirable vascular occlusion. Such methods are well known to physicians who treat such conditions. For example, in myocardial disease these methods include a variety of imaging techniques (e.g., radiotracer methodologies such as $^{99m}$Tc-sestamibi scanning, x-ray, and MRI scanning) and physiological tests. Therefore, induction of angiogenesis in tissue affected by or at risk of being affected by a vascular occlusion is an effective means of preventing and/or attenuating ischemia in such tissue. As a result, although any suitable tissue can be targeted for the induction of angiogenesis, the target tissue is preferably one which is affected by or at risk of being affected by a vascular occlusion.

For example, the blood supply to discrete organs (that are target locations and/or angiogenically dysfunctional locations in the context of the present invention) such as the brain, heart, pancreas, limbs, or generalized areas of the body, such as a foot, can be attenuated by disease, trauma, surgery, or other events. The alleviation of such attenuated blood supply regardless of its origin is contemplated by the present invention. Thus, prevention or alleviation of damage from indications such as myocardial ischemia and stroke are fully contemplated. Additionally, the planning of a surgical procedure can be predictive of the interruption of blood supply through a particular portion of a patient's vasculature. Prior treatment according to the present method can substantially improve the desired outcome of these surgeries. In that case, treatment preferably occurs about one day to about six weeks before the surgery, and more preferably about two to about fourteen days prior to surgery.

Administration of Angiogenic Mediator

The induction of angiogenesis via the systemic administration of angiogenic mediator, such as VEGF protein, can lead to promiscuous induction of angiogenesis which, for example, can cause blindness and increase the aggressiveness of tumor cells. In order to attenuate or prevent such negative side-effects, it is desirable to induce angiogenesis only in the tissue which requires it (i.e., the target location or target tissue) and to minimize the amount of angiogenic mediator that is required for application to other locations.

The present invention involves establishing a gradient of an angiogenic mediator of increasing concentration from a source location in the host to a target location in the host, such that the level of perfusion of blood to the target location in the host is enhanced. While any suitable means of administering the angiogenic mediator to the target tissue that creates a gradient of increasing concentration from the source location to the target location can be used within the context of the present invention, preferably such an administration to produce the gradient in the host between the source and target locations is accomplished by directly administering (e.g., injecting or topically administering) the angiogenic mediator into or near the source location or by topical administration to or near the source and target locations.

By the term "injecting," it is meant that the angiogenic mediator is forcefully introduced into the target tissue. The angiogenic mediator to be injected can be any suitable angiogenic mediator conducive to such administration, including gene transfer vectors such as the adenoviral vectors described herein. Any suitable injection device can be used within the context of the present invention. For example, in the context of direct injection of an angiogenic mediator that comprises an adenoviral vector comprising a DNA encoding an angiogenic substance, a suitable injection device that is capable of delivering simultaneous multiple injections is described in U.S. Pat. No. 5,846,225.

Other suitable injection devices which can be used within the context of the present invention include minimally invasive injection devices. Such devices are capable of accessing a tissue (e.g., the heart) through small incisions of less than about 15 cm and are designed to provide injections through a single lumen, in contrast to the multiple injection devices described above. To allow for the need for multiple injections with a specific geometry, a marking system can be employed so that the sites of previous injections are well delineated. Minimally invasive injection devices can comprise injector tips which are flexible and steerable to allow access via small incisions to the curved outer surface of the heart, for example, which exists at varying angles with respect to the limited aperture window required with minimally invasive surgeries. Suitable minimally invasive injection devices also are described in International Patent Application WO 99/44656.

Furthermore, the angiogenic mediator can be administered to any suitable surface, either internal or external, of (or near to) the source and/or target locations. For example, with respect to directly injecting an angiogenic mediator comprising an adenoviral vector (as described herein) into cardiac tissue, it is contemplated that such an injection can be administered from any suitable surface of the heart (i.e., endocardially and/or epicardially).

While the administration of the angiogenic mediator to form the concentration gradient of the present invention can be performed in any suitable manner (including methods that may include single applications (e.g., injections) of the angiogenic mediator), it is preferred that the concentration gradient be established by at least two injections of the angiogenic mediator. For example, an injection of an angiogenic mediator at a relatively lower concentration at (or near) the source location and another injection of a relatively higher concentration at the target location will produce such a gradient. Similarly, application of a relatively greater volume of a composition comprising an angiogenic mediator at a uniform concentration at (or near) the source location and a similar application of a lesser volume of a composition comprising an angiogenic mediator at (or near) the target location also will generate a suitable gradient.

Alternatively, the present invention can be performed by manipulating multiple applications (e.g., injections), wherein each injection is of a relatively uniform volume of a composition having a relatively uniform concentration of an angiogenic mediator therein. The multiple applications can be 2, 3, 4, 5, or more applications, preferably 5 or more applications, more preferably 8 or more applications, and most preferably at least 10 (e.g., 10, 15, 20, 25, 30 or more) applications. The manipulation of the multiple applications (e.g., injections) to achieve a gradient can be accomplished by modifying the number and/or spacing of the multiple applications (e.g., injections).

Multiple applications provide an advantage over single applications in that they can be manipulated by such parameters as a specific geometry defined by the source and/or target locations, as well as the area therebetween, where each application is administered. The administration of a single dose of the angiogenic mediator via multiple applications can be better controlled, and the effectiveness with which any given dose is administered can be maximized. Moreover, the effectiveness of generating the concentration gradient can be maximized, while the area of the host that is exposed to the angiogenic mediator can be minimized, or at least more localized.

Thus, for example, with regard to the use of an adenoviral vector (comprising a DNA encoding an angiogenic substance as described herein) as the angiogenic mediator, the method of present invention can comprise administering different amounts of the adenoviral vector at a uniform concentration by modifying the number of applications of the adenoviral vector to the host to produce the gradient. More particularly, such an embodiment of the invention comprises administering fewer applications (or doses) of the adenoviral vector at (or near) the source location than at (or near) the target location to produce a gradient.

The specific geometry of the multiple applications is defined by the location on the target and/or source locations, either in two- or three-dimensional space, where each application of the angiogenic mediator is administered. The multiple applications preferably are spaced such that the points of application are separated by up to about 4 cm (e.g., about 0.5–4 cm), more preferably up to about 3 cm (e.g., about 1–3 cm), and most preferably up to about 2 cm (e.g., about 1–2 cm). With respect to the specific geometry of the multiple applications in two-dimensional space, the specific geometry is defined by a plane (i.e., a cross-section of the target tissue) in which the multiple applications lie. The plane defined by the multiple applications can lie at a constant distance from the surface of source and/or target locations (i.e., substantially parallel to the surface of the source and/or target locations), the depth of the plane, or, alternatively, the plane can lie at an angle with respect to the surface of the target and/or source locations. Preferably, a single application will be administered for about every 0.5–15 $cm^2$ of the plane, more preferably for about every 1–12 $cm^2$ of the plane, and most preferably for about every 1.5–7 $cm^2$ of the plane. The depth of the plane is preferably about 1–10 mm, more preferably about 2–7 mm, and most preferably about 3–5 mm. In three-dimensional space, a single application preferably is administered for up to about 50 $cm^3$ (e.g., about 0.5–50 $cm^3$) of source and/or target locations (e.g., source and/or target tissues), more preferably for up to about 35 $cm^3$ (e.g., about 1–35 $cm^3$) of source and/or target locations, and most preferably for up to about 15 $cm^3$ (e.g., about 3–15 $cm^3$) of source and/or target locations. Furthermore, the multiple applications can define any suitable pattern or specific geometry. Therefore, for example, in two-dimensional space, the multiple applications can define a square whereas in three-dimensional space the multiple applications can define a cube.

Another parameter of the multiple applications which can be manipulated is the time differential between each application. Preferably, each of the multiple applications is administered within about 10 minutes (e.g., about 0.5–10 minutes) of each other, more preferably within about 8 minutes (e.g., about 0.5–8 minutes) of each other, and even more preferably within about 6 minutes (e.g., about 1–6 minutes) of each other. Most preferably, all of the multiple applications of the single dose are administered within the aforementioned time frames. Optimally, each of the multiple applications is administered substantially simultaneously.

By manipulating both the specific geometry and the time differentials of the multiple applications, the induction of angiogenesis in non-targeted tissue can be minimized, while desirably causing angiogenesis to the target location.

When administering the angiogenic mediator to the source and/or target locations (e.g., to source and/or target tissues) it is desirable that the administration is such that the angiogenic mediator is able to contact a region reasonably adjacent to the source and/or target locations, as well as the area therebetween. It is not believed to be necessary to have the angiogenic mediator actually contact the precise sites of the source and the terminus for collateral blood vessel formation. However, within the context of multiple applications of the angiogenic mediator, it is desirable that the specific geometry of the multiple applications be defined to allow the angiogenic mediator to contact or reach a region including the source, the terminus, and the area therebetween for the collateral blood vessel formation, preferably to actually contact the precise sites of the source and the terminus for the collateral blood vessel formation, along with the area therebetween.

Furthermore, administration of the angiogenic mediator to the source and/or target locations (which are located within or near the tissue of interest) can be accomplished either in vivo or ex vivo. Therefore, for example, the tissue of interest can be removed from the recipient of the present inventive method, can be treated with the angiogenic substance, and then can be reimplanted into the recipient. Ex vivo administration of the angiogenic mediator to the tissue of interest also helps to minimize undesirable induction of angiogenesis in non-targeted tissue.

The angiogenic mediator desirably is administered to the host in a pharmaceutical composition which comprises a pharmaceutically acceptable carrier and the angiogenic mediator. Any suitable pharmaceutically acceptable carrier can be used within the context of the present invention, and such carriers are well known in the art. The choice of carrier will be determined, in part, by the particular site to which the composition is to be administered and the particular method used to administer the composition. Various examples of suitable pharmaceutical carriers, particularly with regards to pharmaceutically acceptable carriers in combination with adenoviral vectors comprising DNA encoding an angiogenic substance are described in International Patent Application WO 98/32859.

The method of the claimed invention can be practiced, and is useful, in a variety of contexts and can be applied to any suitable host. Preferably, the host is a mammalian host, more preferably the host is a human host, and optimally the host is a human host suffering from either, or at risk of suffering from, ischemic conditions and/or vascular occlusion in the target location.

Dosage

The desired dosage (i.e., total dosage to the host) is such that angiogenesis is induced in the target location, e.g., such that there is a therapeutic and/or prophylactic effect on target location. Additionally, the dosage desirably is such that induction of angiogenesis in non-targeted tissue is minimized.

The dosage also will vary depending upon the angiogenic mediator to be administered. For example, when an adenoviral vector is used as an angiogenic mediator, the dosage will vary depending upon the particular vector and DNA encoding the angiogenic substance in the vector. A dose typically will be at least about $1 \times 10^6$ pfu (e.g., $1 \times 10^6$–$1 \times 10^{13}$ pfu) to the target tissue, e.g., a discrete organ, such as a human heart. The dose preferably is at least about $1 \times 10^7$ pfu (e.g., about $1 \times 10^7$–$1 \times 10^{13}$ pfu), more preferably at least about $1 \times 10^8$ pfu (e.g., about $1 \times 10^8$–$1 \times 10^{11}$ pfu), and most preferably at least about $1 \times 10^9$ pfu (e.g., about $1 \times 10^9$–$1 \times 10^{10}$ pfu). The dose typically is for a volume of targeted tissue of about 100 $cm^3$, more typically about 150 $cm^3$. The dose is administered via multiple applications, and, as such, is divided among the multiple applications. Thus, if the dose is administered via 10 administrations, each administration involves about $1 \times 10^5$–$1 \times 10^{12}$ pfu. Preferably, each application involves about $1 \times 10^6$–$1 \times 10^{12}$ pfu, more preferably about $1 \times 10^7$–$1 \times 10^{10}$ pfu, and most preferably about $1 \times 10^8$–$1 \times 10^9$ pfu. For purposes of considering the dose in terms of particle units (pu), also referred to as viral particles, it can be assumed that there are 100 particles/pfu (e.g., $1\times10^{12}$ pfu is equivalent to $1\times10^{4}$ pu). In a single round of vector administration, using, for example, an adenoviral vector deleted of the entire E1a region, part of the E1b region, and part of the E3 region of the adenoviral genome, wherein the vector carries human $VEGF_{121}$ or $VEGF_{165}$ under the control of a standard CMV immediate early promoter, about $10^{7}$–$10^{13}$ pfu, preferably about $10^{9}$–$10^{11}$ pfu, are administered to the host (e.g., to a discrete organ containing the source and/or target locations) with an estimated volume of about 150 cm$^3$. Under these conditions, a substantial level of VEGF production is achieved in the tissue of interest without producing detectable levels of VEGF production in distal tissues.

All of the references cited herein, including patents, patent applications, and publications, are hereby incorporated in their entireties by reference. The use of the terms "a" and "an" to describe any element of the claimed invention (e.g., "an adenoviral vector" or "a DNA") should be construed so as to include both singular and plural forms of the referenced element unless stated or made clear otherwise herein.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A method of directing blood vessel growth from a source location to a target location in a mammalian host, the method comprising directly administering an angiogenic mediator to a target location and a source location in an organ or a tissue, wherein the amount of angiogenic mediator administered at the target location is greater than the amount of angiogenic mediator administered at the source location, such that a gradient of the angiogenic mediator of increasing concentration from the source location to the target location is established, whereby blood vessel growth is directed from the source location to the target location, and wherein the angiogenic mediator is an angiogenic peptide or a nucleic acid encoding an angiogenic peptide.

2. The method of claim 1, wherein the target location is an angiogenically dysfunctional location.

3. The method of claim 2, wherein the angiogenically dysfunctional location is affected by a vascular occlusion.

4. The method of claim 3, wherein the angiogenically dysfunctional location is in a heart.

5. The method of claim 2, wherein the angiogenically dysfunctional location is suffering from ischemia.

6. The method of claim 5, wherein the angiogenically dysfunctional location is in a heart.

7. The method of claim 1, wherein the angiogenic mediator is a nucleic acid encoding an angiogenic peptide positioned within a replication deficient adenoviral vector.

8. The method of claim 7, wherein the angiogenic peptide is selected from the group consisting of $VEGF_{121}$, $VEGF_{145}$, $VEGF_{165}$, and $VEGF_{189}$.

9. The method of claim 8, wherein the angiogenic peptide is $VEGF_{121}$.

10. The method of claim 7, wherein the adenoviral vector is deficient in at least one essential gene function of the E4 region of the adenoviral genome.

11. The method of claim 10, wherein the adenoviral vector has at least a partial deletion of the E1 region of the adenoviral genome, at least a partial deletion of the E3 region of the adenoviral genome, and at least a partial deletion of the E4 region of the adenoviral genome.

12. The method of claim 7, wherein the nucleic acid encoding an angiogenic peptide is oriented from right to left in the adenoviral genome of the adenoviral vector.

13. The method of claim 7, wherein the adenoviral vector is deficient in at least one essential gene function of the E1 region of the adenoviral genome.

14. The method of claim 13, wherein the nucleic acid encoding an angiogenic peptide is positioned in the E1 region of the adenoviral genome of the adenoviral vector.

15. The method of claim 14, wherein the adenoviral vector is deficient in at least part of the E3 region of the adenoviral genome.

16. The method of claim 14, wherein the adenoviral vector has at least a partial deletion of the E1a region of the adenoviral genome, at least a partial deletion of the E1b region of the adenoviral genome, and at least a partial deletion of the E3 region of the adenoviral genome.

17. The method of claim 1, wherein the host is a human.

18. The method of claim 1, wherein the angiogenic mediator is administered to the target location and the source location within about 10 minutes.

19. The method of claim 1, wherein the angiogenic mediator is a nucleic acid encoding an angiogenic peptide.

20. The method of claim 19, wherein the nucleic acid encodes a VEGF.

21. The method of claim 20, wherein the VEGF is $VEGF_{121}$.

* * * * *